(12) United States Patent
Pacetti

(10) Patent No.: US 7,255,891 B1
(45) Date of Patent: *Aug. 14, 2007

(54) METHOD FOR COATING IMPLANTABLE MEDICAL DEVICES

(75) Inventor: Stephen D. Pacetti, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 476 days.

This patent is subject to a terminal disclaimer.

(21) Appl. No.: 10/375,497

(22) Filed: Feb. 26, 2003

(51) Int. Cl.
*B05D 1/00* (2006.01)
*A61L 27/00* (2006.01)

(52) U.S. Cl. .................... 427/2.24; 427/2.25; 427/2.28

(58) Field of Classification Search .............. 427/2.24, 427/2.25, 2.28, 370
See application file for complete search history.

(56) References Cited

U.S. PATENT DOCUMENTS

| | | | |
|---|---|---|---|
| 4,977,901 A | 12/1990 | Ofstead | |
| 5,112,457 A | 5/1992 | Marchant | |
| 5,328,471 A | 7/1994 | Slepian | |
| 5,455,040 A | 10/1995 | Marchant | |
| 5,464,650 A | 11/1995 | Berg et al. | |
| 5,505,984 A * | 4/1996 | England et al. | 427/2.24 |
| 5,578,073 A | 11/1996 | Haimovich et al. | |
| 5,599,576 A * | 2/1997 | Opolski | 427/2.3 |
| 5,605,696 A | 2/1997 | Eury et al. | |
| 5,667,767 A | 9/1997 | Greff et al. | |
| 5,670,558 A | 9/1997 | Onishi et al. | |
| 5,679,400 A * | 10/1997 | Tuch | 427/2.14 |
| 5,700,286 A | 12/1997 | Tartaglia et al. | |
| 5,716,981 A | 2/1998 | Hunter et al. | |
| 5,762,944 A * | 6/1998 | Inoue et al. | 424/400 |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,873,904 A | 2/1999 | Ragheb et al. | |
| 5,879,878 A * | 3/1999 | Raguse et al. | 435/4 |
| 5,971,954 A | 10/1999 | Conway et al. | |
| 5,980,928 A | 11/1999 | Terry | |
| 5,980,972 A | 11/1999 | Ding | |
| 6,015,541 A | 1/2000 | Greff et al. | |
| 6,042,875 A | 3/2000 | Ding et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,066,584 A * | 5/2000 | Krell et al. | 501/127 |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,129,761 A | 10/2000 | Hubbell | |
| 6,143,037 A * | 11/2000 | Goldstein et al. | 424/422 |
| 6,153,252 A | 11/2000 | Hossainy et al. | |
| 6,165,212 A | 12/2000 | Dereume et al. | |
| 6,235,340 B1 * | 5/2001 | Lee et al. | 427/2.12 |
| 6,265,016 B1 * | 7/2001 | Hostettler et al. | 427/2.11 |
| 6,270,831 B2 * | 8/2001 | Kumar et al. | 427/2.24 |
| 6,428,616 B1 * | 8/2002 | Neely, Jr. | 106/628 |
| 6,451,373 B1 * | 9/2002 | Hossainy et al. | 427/2.25 |
| 6,596,402 B2 * | 7/2003 | Soerens et al. | 428/447 |
| 6,607,598 B2 * | 8/2003 | Schwarz et al. | 118/500 |
| 6,656,216 B1 * | 12/2003 | Hossainy et al. | 623/1.13 |
| 6,716,444 B1 * | 4/2004 | Castro et al. | 424/422 |
| 6,746,482 B2 * | 6/2004 | Ung-Chhun | 623/1.46 |
| 6,844,028 B2 * | 1/2005 | Mao et al. | 427/384 |
| 2002/0065551 A1 * | 5/2002 | Koole et al. | 623/1.25 |
| 2003/0054431 A1 * | 3/2003 | Raguse et al. | 435/25 |
| 2004/0194704 A1 * | 10/2004 | Chappa et al. | 118/719 |
| 2004/0208985 A1 * | 10/2004 | Rowan et al. | 427/2.25 |
| 2004/0241325 A1 * | 12/2004 | Al.Lamee et al. | 427/299 |
| 2006/0024426 A1 * | 2/2006 | Akerman et al. | 427/2.1 |
| 2006/0128739 A1 * | 6/2006 | Maryanoff et al. | 514/291 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

* cited by examiner

*Primary Examiner*—Bret Chen
(74) *Attorney, Agent, or Firm*—Squire, Sanders & Dempsey LLP

(57) ABSTRACT

A method for coating an implantable medical device that has the steps of applying a polymer composition onto the device, the polymer composition including a solution of a polymer in a solvent, and drying the polymer composition for a period of time at a drying temperature higher than the room temperature in an environment having relative humidity between about 20% and about 100%.

17 Claims, No Drawings

METHOD FOR COATING IMPLANTABLE MEDICAL DEVICES

BACKGROUND OF THE INVENTION

1. Field of the Invention

This invention relates to methods for coating drug delivery devices. More specifically, the invention is directed to applying a composition onto an implantable medical device and drying the composition at an elevated temperature in an environment having increased relative humidity.

2. Description of the Background

In the field of medical technology, there is frequently a necessity to administer drugs locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results.

One commonly applied technique for local delivery of the drug is through the use of medicated stents. One method of medicating a stent is with the use of a polymer coating incorporating a drug. To fabricate the polymer coating, a suitable polymer is usually dissolved in a solvent or blend of solvents, followed by applying the solution onto the stent, for example, by spraying or dipping. To complete the process of fabricating the stent coating, the stent is dried and/or baked to remove the solvent.

Examples of solvents currently used to dissolve biocompatible polymers for fabricating stent coatings include dimethylacetamide (DMAC), dimethylsulfoxide (DMSO), dimethylformamide (DMF), and formamide. These solvents or similar solvents with relatively high boiling points, for example, above 120° C. at ambient pressure, and/or low volatility, for example, having vapor pressure under 15 Torr at room temperature, have a tendency to evaporate very slowly. Prolonged period of time may be needed to allow the solvent to fully evaporate from the coating because residual or trace amounts of the solvent may remain in the coating composition, which may produce an adverse response subsequent to the stent implantation. Baking of the stent at relatively high temperatures may be needed to facilitate the process of the solvent removal. The baking temperatures used for this purpose, should not exceed the temperature at which the drug can be adversely affected, however. The embodiments of the present invention provide methods for facilitating the evaporation of the solvent from the coating composition.

SUMMARY

A method for coating an implantable medical device is provided, the method comprises applying a polymer composition onto the device, the polymer composition including a solution of a polymer in a solvent, and drying the polymer composition for a period of time at a drying temperature higher than the room temperature in an environment having relative humidity between about 20% and about 100%. The drying temperature can be between about 30° C. and about 110° C. The drying time can be between about 10 minutes and about 240 minutes. The polymers absorbing at least about 1 mass % or more of water when exposed to relative humidity of about 100% can be used to make the polymer compositions. One example of the polymer that can be used is poly(ethylene-co-vinyl alcohol). The solvents having a boiling point greater than about 120° C. at atmospheric pressure, or having a vapor pressure at 20° C. of less than about 15 Torr, or both can be used to make the polymer compositions. Examples of the solvents that can be used include dimethylacetamide, dimethylsulfoxide, dimethylformamide, and formamide.

DETAILED DESCRIPTION

A coating for an implantable medical device, such as a stent, can include an optional primer layer, a drug-polymer layer, and an optional topcoat layer. The drug-polymer layer can be applied directly onto the stent surface to serve as a reservoir for an active agent or a drug which is incorporated into the drug-polymer layer. An optional primer layer can be applied between the stent and the drug-polymer layer to improve the adhesion of the drug-polymer layer to the stent. An optional topcoat layer can be used to reduce the rate of release of the drug from the reservoir.

To fabricate a stent coating, a polymer, for example, a polymer can be dissolved in a solvent or in a system comprising a mixture of solvents to form the polymer solution. One example of a suitable polymer is poly(ethylene-co-vinyl alcohol)(EVAL). The polymer solution can then be applied onto the surface of the stent by a conventional method, e.g., by spraying or dipping, to form the coating. In one embodiment, the solvent can have boiling point greater than about 120° C., for example, above about 130° C. at atmospheric pressure. In another embodiment, the solvent can have vapor pressure at 20° C. of less than about 15 Torr, for example, below about 10 Torr. In yet another embodiment, the solvent can have both boiling point and vapor pressure described above.

Examples of solvents that can be used with EVAL include DMAC, DMSO, DMF, formamide, N-methyl-2-pyrrolidone (NMP), sulfolane, benzyl alcohol, cyclohexanol, phenol, formic acid, m-cresol, p-cresol, trifluoroacetic acid, glycerol, ethylene glycol, propylene glycol, and mixtures thereof.

The concentration of EVAL in the polymer solution can be between about 1 and 5 mass %, for example, about 2 mass %. An EVAL solution can be prepared by combining EVAL with a solvent or a mixture of solvents described above and by stirring the composition for about 2 to 4 hours at a temperature between about 75° C. and about 85° C., for example, about 80° C. EVAL can be used to manufacture of the primer layer, drug-polymer layer, and/or the topcoat layer.

The polymer solution can be then applied on the stent by a commonly known technique known to those having ordinary skill in the art. For example, the primer layer, the drug-polymer layer and/or the topcoat layer can be consecutively applied by spraying or dipping, followed by drying, for example, by baking. The baking can be also done between applying of each layer. According to embodiments of the present invention, the coating can be baked in an oven at an elevated temperature, while the oven environment has a high relative humidity. The baking temperature can be within a range of between about 30° C. and about 110° C., for example, about 80° C.

The high humidity atmosphere can be created in the baking oven, for example, by having a tray or pan of water inside the oven, spraying or misting water inside the oven, or passing into the oven a water fog or mist that is generated outside the oven. The elevated humidity can be created during, and/or prior to, the baking process. The relative humidity of the oven environment where the stent coating is baked can be within a range of between about 20% and about 100%, for example about 60%. The baking time can be between about 10 minutes and about 240 minutes, for example, about 30 minutes. Among other benefits, the method of forming the stent coating according to embodiments of the present invention allows for faster drying time without substantial increase in the baking temperature. It is believed that this process will facilitate elimination of any residual or trace amounts of the solvent from the coating.

In addition to EVAL, the formulation for making the drug-polymer layer can additionally include an active agent or a drug which can be incorporated into the EVAL solution. The amount of the drug can be between about 0.1 and about 10 mass % of the total mass of the formulation used to make the drug-polymer layer. The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany), methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The method of the present invention can be used for fabricating stent coatings including polymers that absorb at least about 1 mass % of water when exposed to relative humidity of about 100%. EVAL, which absorbs up to 5 mass % of water when exposed to relative humidity of about 100%, is just one example of a polymer that can be used. Examples of suitable polymers other than EVAL include poly(N-vinylpyrrolidone)(PVP), ethyl cellulose, cellulose acetate, carboxymethyl cellulose, cellulosics, chitin, chitosan, poly(vinyl alcohol), heparin, dextran, dextrin, dextran sulfate, collagen, gelatin, hyaluronic acid, chondroitan sulfate, glycosaminoglycans, poly[(2-hydroxyethyl)methylmethacrylate], polyurethanes, poly(ether urethanes), poly(ester urethanes), poly(carbonate urethanes), thermoplastic polyesters, solvent soluble nylons, poly(acrylamide), poly(acrylic acid), copolymers of acrylic acid and acrylates, poly(methacrylic acid), copolymers of methacrylic acid and methacrylates, and blends thereof. Table 1 is a summary demonstrating which solvents can be used in conjunction with particular polymers in order to fabricate coatings according to embodiments of the present invention.

TABLE 1

Examples of Polymer-Solvent Compositions

| Example | Polymer | Solvents |
| --- | --- | --- |
| 1 | EVAL | DMSO, DMAC, DMF, NMP, formamide, cyclohexanol, sulfolane, benzyl alcohol, phenol, formic acid, m-cresol, p-cresol, trifluoroacetic acid, glycerol, ethylene glycol, propylene glycol |
| 2 | Sodium Heparin | DMSO, DMAC, DMF, NMP, formamide, benzyl alcohol |
| 3 | PVP | Propylene glycol, ethylene glycol, formamide, glycerol, DMSO |
| 4 | Hyaluronic Acid | DMF, DMSO, formamide |
| 5 | Poly(vinyl alcohol) | DMSO, formamide |
| 6 | TECOFLEX 80A poly(ester urethane) | DMAC, DMF |

The method of the present invention has been described in conjunction with a stent. However, the coating can also be used with a variety of other medical devices. The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Some embodiments of the present invention are illustrated by the following Examples.

EXAMPLE 1

A polymer solution containing about 4.0 mass % EVAL and the balance, a solvent blend of DMAC and pentane, with a mass ratio between DMAC and pentane of about 4:1 can be prepared. To prepare the polymer solution, EVAL can be combined with DMAC and the mixture can be stirred for about 2 hrs at a temperature of about 80° C. The solution can be applied onto a 13-mm TETRA stent (available from Guidant Corp.) to form a primer layer. To apply the primer layer, a spray apparatus, such as an EFD 780S spray nozzle with a VALVEMATE 7040 control system, manufactured by EFD, Inc. of East Providence, R.I. can be used. The EFD 780S spray nozzle is an air-assisted external mixing atomizer. The composition can be atomized by air and applied to the stent surfaces. The atomization pressure can be about 0.1 MPa (15 psi). During the process of applying the composition, the stent can be rotated about its longitudinal axis, at a speed of about 120 rpm. The stent can be also linearly moved along the same axis during the application.

The EVAL solution can be applied to the 13-mm TETRA in a series of 10-second passes, to deposit about 10 µg of coating per spray pass. Instead of the 13-mm TETRA stent, other suitable stents can also be used, for example, a 12-mm VISION stent (also available from Guidant Corporation). Between the spray passes, the stent can be dried for about 10 seconds using flowing air with a temperature of about 60° C. Five spray passes can be applied, followed by baking the primer layer in an oven. As the primer layer contains no active agent, the primer layer can be baked at a temperature at about 140° C. for about 1 hour. Optionally, the relative humidity in the oven during baking can be about 60%. As a result, a primer layer can be formed having a solids content of about 50 µg. "Solids" means the amount of the dry residue deposited on the stent after all volatile organic compounds (e.g., the solvent) have been removed.

A drug-containing formulation can be prepared comprising about 4.0 mass % EVAL, about 1.33 mass % EVEROLIMUS, and the balance, a solvent blend, the blend comprising DMAC and pentane in a mass ratio of about 4:1. EVAL can be combined with DMAC and the mixture can be stirred for about 2 hrs at a temperature of about 80° C. Pentane and EVEROLIMUS can then be added to the EVAL solution.

The drug-containing formulation can be sprayed to the primed stent. In a manner identical to the application of the primer layer, 26 spray passes can be performed, depositing about 20 µg of the wet drug-polymer layer per each pass. The wet drug-polymer layer can then be baked in an oven at about 50° C. for about 1 hour, while relative humidity in the oven is maintained at about 60%, to form the dry drug-polymer layer having a solids content of about 460 µg.

EXAMPLE 2

A primer solution can be prepared and coated onto a 13 mm TETRA stent as described in Example 1. A drug-containing formulation can be prepared comprising about 4.0 mass % EVAL, about 2.0 mass % paclitaxel, and the balance, a solvent blend of DMAC and tetrahydrofuran (THF), the blend having a mass ratio between DMAC and THF of about 3:2. EVAL can be combined with DMAC and the mixture stirred for about 2 hours at a temperature of about 80 C. THF and paclitaxel can then be added to the EVAL solution.

The drug containing formulation can be sprayed onto the primed stent. In a manner identical to the application of the primer layer, nine spray passes can be performed, depositing about 20 µg of the wet formulation per each spray pass. The wet drug-polymer layer can then be baked in an oven at about 60° C. for about one hour, while the relative humidity in the oven is maintained at about 60%, to form a the drug-polymer layer having a solids content of about 150 µg.

A topcoat formulation can be prepared comprising about 2.2 mass % EVAL, about 1.5 mass % sodium heparin, and the balance, a solvent blend of formamide, methanol and DMAC, the blend having a mass ratio between formamide, methanol and DMAC of about 1:1:3. EVAL can be combined with DMAC and the mixture can be stirred for about 2 hours at a temperature of about 80° C. Sodium heparin can be dissolved in the blend of formamide and methanol. The EVAL solution can then be added to the heparin solution. This topcoat formulation can be sprayed onto the dry drug-polymer layer. In a manner identical to the application of the primer and drug-polymer layers, four spray passes can be performed, depositing about 20 µg of the wet topcoat per spray pass. The wet topcoat layer can then be baked in an oven at about 60° C. for about one hour, while the relative humidity in the oven is maintained at about 60%, to form a topcoat layer having a solids content of about 60 µg.

EXAMPLE 3

A polymer solution containing about 2.0 mass % of poly(butyl methacrylate)(PBMA) and the balance, a blend of acetone and xylene having a mass ratio between acetone and xylene of about 3:2 can be prepared. To prepare the polymer solution, PBMA can be combined with acetone and the mixture can be stirred for about 1 hour at 60° C., followed by adding xylene. The solution can be sprayed onto a stent to form a primer layer as described in Example 1. The PBMA solution can be applied to a 13-mm TETRA stent in a series of 10-second passes, to deposit about 10 µg of the polymer solution per spray pass. Between passes, the stent can be dried at ambient temperature for about 10 seconds using flowing air. Five spray passes can be applied, followed by baking the wet primer layer in an oven at about 80° C. for about 30 minutes. As a result, a primer layer can be formed having a solids content of about 50 µg.

A drug-containing formulation can be prepared comprising about 4.0 mass % BIONATE 55D, about 2.0 mass % rapamycin, and the balance, a solvent blend of DMAC and THF, the blend having a mass ratio between DMAC and THF of about 1:1. BIONATE 55D is a trade name of a thermoplastic polycarbonate-urethane elastomer formed as the product of the reaction between a hydroxyl-terminated polycarbonate, an aromatic diisocyanate, and a low molecular weight glycol used as a chain extender. BIONATE 55D is available from The Polymer Technology Group Incorporated of Berkeley, Calif. BIONATE 55D can be combined with DMAC and the mixture can be stirred for about 6 hrs at a temperature of about 80° C. THF and rapamycin can then be added to the BIONATE 55D solution.

The drug containing formulation can be sprayed onto the primed stent. In a manner identical to the application of the primer layer, 27 spray passes can be performed, depositing about 20 µg per spray pass. The wet drug-polymer layer can then be baked in an oven at about 60° C. for about one hour, while the relative humidity in the oven is maintained at about 60%, to form a the drug-polymer layer having a solids content of about 500 µg.

EXAMPLE 4

A primer solution can be prepared and coated onto a 13 mm TETRA stent as described in Example 1. A drug-containing formulation can be prepared and coated on the stent as described in Example 2, except the baking of the wet drug-polymer layer can be carried out at about 100% relative humidity in a sealed vessel. First, a sealed vessel containing deionized water can be placed in an oven set to about 50° C. and allowed to equilibrate. The stent having wet drug-polymer layer coated thereon can be placed into the vessel, followed by closing the vessel and baking at about 50° C. for two hours. The stent is positioned in the vessel in such as way as to not make contact with the deionized water.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for coating an implantable medical device, comprising:
    (a) applying a polymer composition onto the device, the polymer composition including a solution of a polymer in a solvent wherein the solvent comprises a solvent having a boiling point greater than about 120° C. at atmospheric pressure and/or wherein the solvent comprises a solvent having a vapor pressure less than about 15 Torr at 20° C.; and
    (b) drying the polymer composition for a period of time at a drying temperature between 30° C. and 110° C. in an environment having relative humidity between about 20% and about 100%.

2. The method of claim 1, wherein the implantable medical device is a stent.

3. The method of claim 1, wherein the relative humidity is about 60%.

4. The method of claim 1, wherein the drying temperature is about 80° C.

5. The method of claim 1, wherein the polymer absorbs about 1 mass % or more of water when exposed to relative humidity of about 100%.

6. The method of claim 5, wherein the polymer absorbs about 5 mass % of water.

7. The method of claim 1, wherein the polymer comprises a vinyl polymer, an acrylic polymer, a urethane-based polymer, a polyester, or a polysaccharide.

8. The method of claim 7, wherein the acrylic polymer is selected from a group consisting of poly[(2-hydroxyethyl) methylmethacrylate], poly(acrylamide), poly(acrylic acid), copolymers of acrylic acid and acrylates, poly(methacrylic acid), copolymers of methacrylic acid and methacrylates, and blends thereof.

9. The method of claim 1, wherein the solvent comprises a solvent having a boiling point greater than about 130° C. at atmospheric pressure.

10. The method of claim 1, wherein the solvent comprises a solvent having a vapor pressure less than about 10 Torr at 20° C.

11. The method of claim 1, wherein the solvent is selected from a group consisting of dimethylacetamide, dimethylsulfoxide, dimethylformamide, formamide, N-methyl-2-pyrrolidone, sulfolane, benzyl alcohol, cyclohexanol, phenol, formic acid, m-cresol, p-cresol, trifluoroacetic acid, glycerol, ethylene glycol, propylene glycol, xylene and mixtures thereof.

12. The method of claim 1, wherein the drying time is between about 10 minutes and about 240 minutes.

13. The method of claim 1, wherein the composition additionally comprises a therapeutic substance.

14. A method for coating an implantable medical device, comprising:
    (a) applying a coating material including a polymer and a solvent to the device wherein the solvent comprises a solvent having a boiling point greater than about 120° C. at atmospheric pressure and/or wherein the solvent comprises a solvent having a vapor pressure less than about 15 Torr at 20° C.; and
    (b) drying the coating material in an oven for a period of time at a drying temperature between 30° C. and 110° C., wherein the oven has a relative humidity between about 20% and about 100%.

15. The method of claim 14, wherein the relative humidity is between about 60% and about 100%.

16. The method of claim 14, wherein the device is a stent.

17. The method of claim 14, wherein the coating material additionally comprises a drug.

* * * * *